US005665707A

United States Patent [19]
Remington et al.

[11] Patent Number: 5,665,707
[45] Date of Patent: Sep. 9, 1997

[54] TREATMENT FOR TOXOPLASMOSIS WITH A COMPOSITION COMPRISING A LINCOSAMIDE AND A SPIROPIPERIDYL DERIVATIVE OF RIFAMYCIK S

[75] Inventors: Jack S. Remington, Menlo Park; Fausto G. Araujo, Palo Alto, both of Calif.

[73] Assignee: Palo Alto Medical Foundation, Palo Alto, Calif.

[21] Appl. No.: 487,721

[22] Filed: Jun. 7, 1995

Related U.S. Application Data

[63] Continuation of Ser. No. 203,539, Feb. 28, 1994, Pat. No. 5,529,994, which is a continuation-in-part of Ser. No. 57,288, May 5, 1993, abandoned.

[51] Int. Cl.$^6$ .......................... A61K 31/70; A61K 31/33
[52] U.S. Cl. ................................. 514/24; 514/183
[58] Field of Search ............................. 514/183, 24

[56] References Cited

U.S. PATENT DOCUMENTS

| | | | |
|---|---|---|---|
| 4,086,225 | 4/1978 | Marsili et al. | 540/453 |
| 4,219,478 | 8/1980 | Marsili et al. | 514/333 |
| 4,327,096 | 4/1982 | Marsili et al. | 514/212 |
| 4,738,958 | 4/1988 | Franco et al. | 514/183 |
| 4,963,531 | 10/1990 | Remington | 514/29 |

OTHER PUBLICATIONS

Windholz et al., The Merck Index, 10th Ed. (1983) p. 335 abstract No. 2321.

Remington, J.S. and Desmonts, G. : In Infectious Diseases of the Fetus and Newborn Infant, 3rd Ed., J.S. Remington, J.O. Klein, eeds Philadelphia: WB Saunders Company (1990) pp. 89–195.

Remington, J.S. et al. "The effect of Rifampin *Toxoplasma gondii*" (1970) Proc. Soc. Ex. Biot. and Med: 135: 167–172.

Singleton, P. and Sainsbury, D. eds. (1987) Dictionary of Microbiology and Molecular Biology, 2nd Ed., John Wiley and Sons, Ltd., Bath (England) p. 769.

Physicians Desk Reference (1993) : pp. 1394–1397.

Woodley, C.L. and Kilburn, J.O. (1982) Am. Rev. Respir. Dis. 126:586–587.

Hoy, J. et al. (1990) J. Infect. Dis. 161: 801–805.

Araujo, F.G. et al. (1993) J. Infect. Dis. 167:494–7.

Ruskin, J. and Remington, J. S. (1976) Ann. Intern. Med. 84:193–199.

O'Brien, R.J. et al. (1987) Review of Infectious Diseases 9:519–529.

Araujo, F.G. (1992) Depletion of CD4+ T Cells But Not Inhibition of the Protective Activity of IFN–γ J. Immunol. 149:3003–3007.

Araujo, F.G. et al. (1991) In Vivo Activity of the Macrolide Eur. J. Clin. Microbiol. Infect. Dis. 10:519–524.

Araujo, F.G. et al. (1992) In Vitro and In Vitro Activities of the Hydroxynaphthoquinone 566C80 Against the Cyst Form of *Toxoplasma gondii* . Antimicrob. Agents Chemother. 36:326–330.

Araujo, F.G. et al. (1991) Remarkable In Vitro and in Vitro Activities of the Hydroxynaphthoquinone 566C80 Against Tachyzoites and Cysts of *Toxoplasma Gondii* . Antimicrob. Agents and Chemother. 35:293–299.

Araujo, F.G. et al. (1992) Clarithromycin—minocycline Is Synergistic in a Murine model of Toxoplasmosis. J. Infect. Dis. 165:788.

Chiodini, R.J. et al. (1993) Use of Rifabutin in Treatment of Systemic Mycobacterium Paratuberculosis Infection in Mice. Antimicrob. Agents Chemother. 37:1645–1648.

Dannemann, B. et al. (1992) Treatment of Toxoplasmic Encephalitis in Patients With Acquired Immunodeficiency Syndrom. Ann. Intern. Med. 116:33–43.

Dannemann, B. et al. (1988) Treatment of Toxoplasmic Encephalitis with Intravenous Clidamycin. Arch. Intern. Med. 148:2477–2482.

Falloon, Judith, Current Therapy for HIV Infection and its Infectious Complications, (1992) Post Graduate Medicine, vol. 91, No. 8, pp. 115–132.

Ellner, J.J. et al. (1991) *Mycobacterium avium* Infection in Aids. J. Infect. Dis. 163:1326–1335.

Heifets, L. B. et al. Bacteriostatic and Bactericidal Effects of Rifabutin (Ansamycin, LM 427) on *Mycobacterium avium* clinical Isolates, pp. 180–183. In M. Casal (ed.) Mycobacteria of Clinical Interest–1986. Amesterdam: Elsevier Science.

Horsburgh, C.R. (1991). *Myobacterium avium* Complex Infections in the Acquired Immunodeficiency Syndrome. N. Engl. J. Med. 324:1332–1338.

Hughes, W.T. et al. (1991) Safety and Pharmacokinetics of 566C80, a Hydroxynaphtoquinone with Anti–*Pneumocystis carinii* Activity. J. Infect. Dis. 163:843–848.

Israelski, D.M. et al. Toxoplasmosis in Patients with AIDS, pp. 241–264 In The Medical Management of AIDS—1990. M.A. Sande and P.A. Volberding (eds.) Philadelphia: W.B. Sounders.

Israelski, D.M. et al. (1989) Treatment with Anti–L3T4 (CD4) Monoclonal Antibody Reduces the Inflammatory Response in Toxoplasmic Encephalitis. J. Immunol. 142:954–958.

Narang, P.K. et al. (1992) Rifabutin Absorption in Humans; Relative Bioavailability and Food Effect. Clin. Pharmac. Therap. 52:335–341.

(List continued on next page.)

*Primary Examiner*—Kevin E. Weddington
*Attorney, Agent, or Firm*—Cooley Godward LLP

[57] ABSTRACT

A method of reducing the severity of toxoplasmosis resulting from infection of a patient with *Toxoplasma gondii* by administering to a patient in need of such treatment, either after infection or before exposure to infection, a therapeutically effective amount of a compound that is a spiropiperidyl derivative of rifamycin S, wherein the derivative comprises an imidazole ring that includes carbons at positions 3 and 4 of the rifamycin ring, the carbon at position 2 of the imidazole ring also being a ring carbon at position 4 of a piperidine ring system, thereby forming a spiropiperidyl ring system, the spiropiperidyl ring system optionally comprising a lower hydrocarbon substituent on the nitrogen of the piperidine.

7 Claims, 6 Drawing Sheets

OTHER PUBLICATIONS

McCabe, R.E. et al. *Toxoplasma gondii*, pp. 2090–2103. In Third ed. Principles and Practice of Infectious Diseases—1990. G.L. Mandell et al. (eds.) London: Churchill Livingstone, Inc.

Hunter, C.A. et al. (1993) Cytokine mRNA in the Central Nervous System of SCID Mice Infected With *Toxoplasma Gondii*. Infect. Immun. 61:4038–4044.

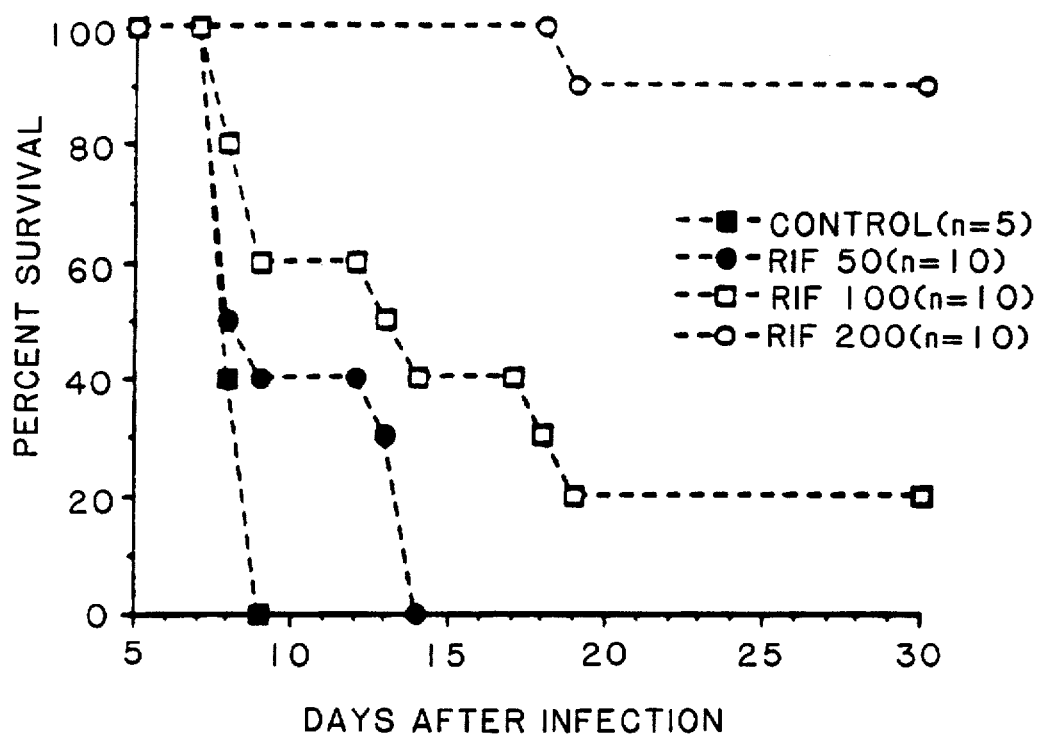
F I G. IA
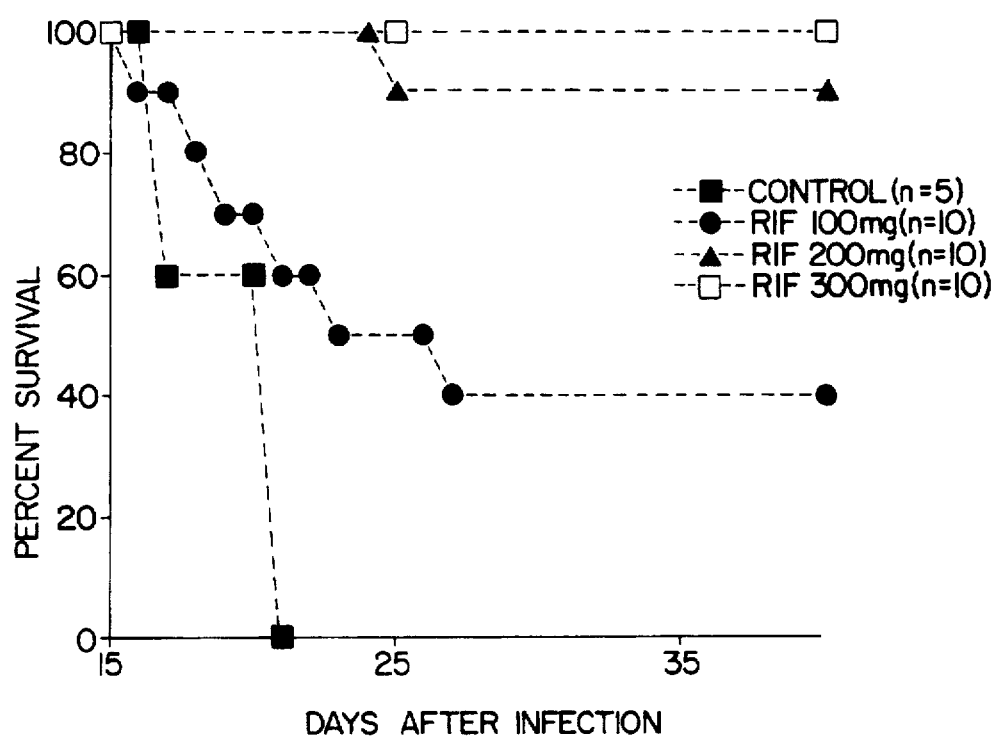
F I G. IB

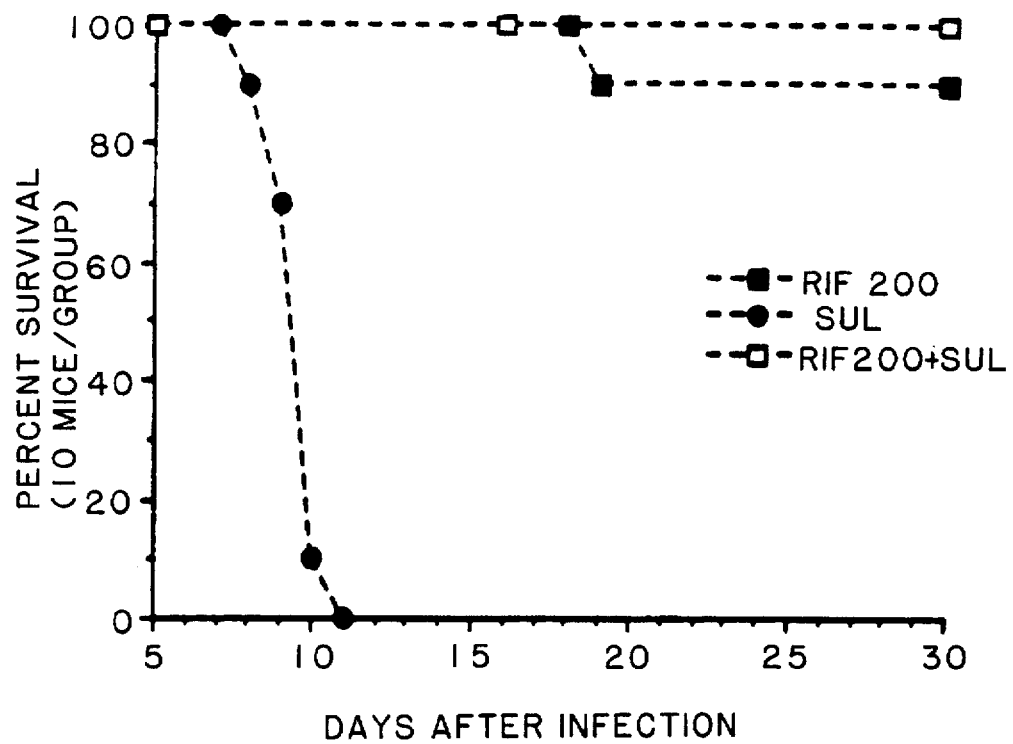
F I G. 4
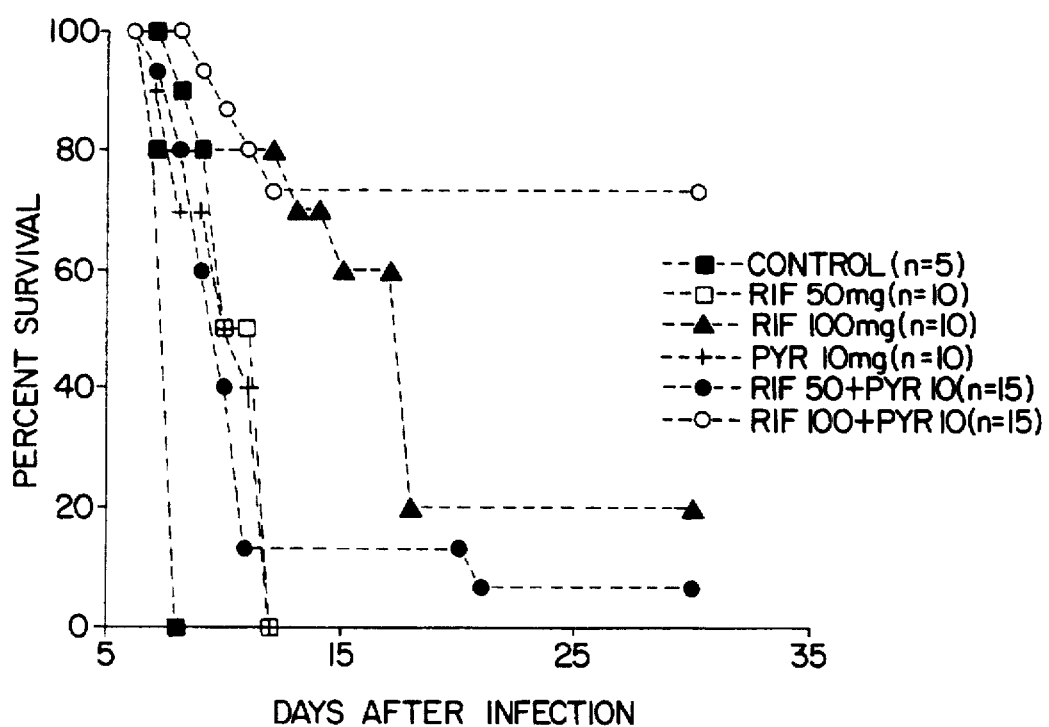
F I G. 5

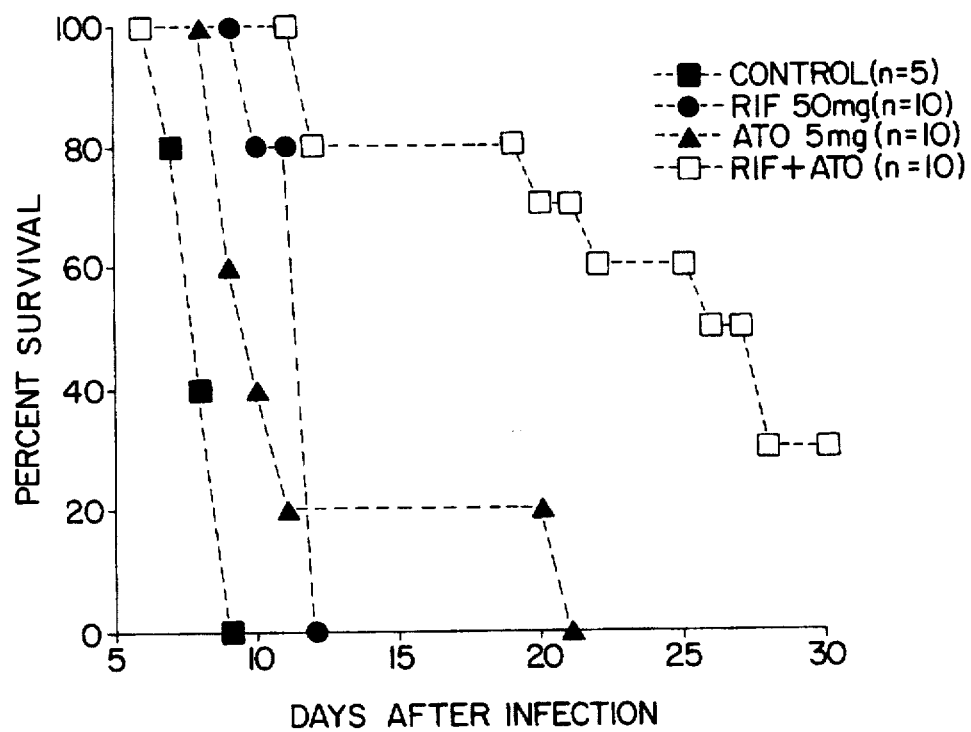
F I G. 7B
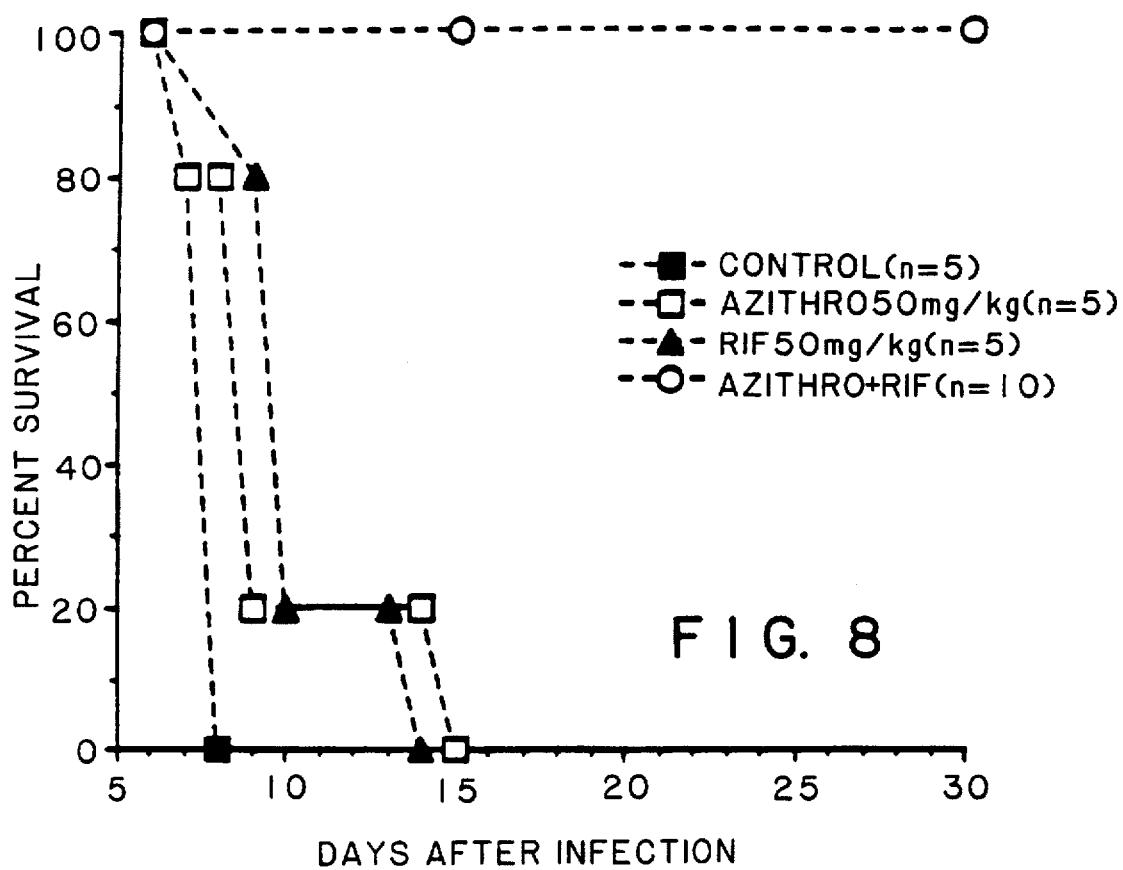
F I G. 8

TREATMENT FOR TOXOPLASMOSIS WITH A COMPOSITION COMPRISING A LINCOSAMIDE AND A SPIROPIPERIDYL DERIVATIVE OF RIFAMYCIK S

CROSS-REFERENCE TO RELATED APPLICATIONS

This application is a continuation of U.S. Ser. No. 08/203,539, filed Feb. 28, 1994, now U.S. Pat. No. 5,529,994 which is a continuation-in-part of application Ser. No. 08/057,288, filed May 5, 1993, now abandoned.

BACKGROUND OF THE INVENTION

1. Field of the Invention

This invention relates to the field of disease treatment and prophylaxis. More particularly it relates to the treatment and prophylaxis of *Toxoplasma gondii* infections.

2. Description of the Background

Toxoplasmosis is caused by the parasitic protozoan, *Toxoplasma gondii*. In humans, the disease is traditionally associated with the developing fetus in whom it can cause severe neurological problems manifesting as hydrocephaly, mental retardation and/or blindness [1, 2]. In healthy adults, the disease is typically mild, producing few if any symptoms. In immunocompromised adults, however, the parasite can cause severe or even fatal disease [3, 4, 5]. The disease also occurs in other mammals and is a leading cause of spontaneous abortion in sheep.

The parasite itself is extremely widespread and is typically acquired through the ingestion of undercooked meat in which tissue cysts containing the parasite may reside. This form is highly infectious if the meat is not well cooked. Alternatively, the parasite can be contracted through ingestion of foods contaminated with oocysts that are shed in the feces of infected cats. The oocyst is the product of the complete sexual cycle. The oocyst form is highly resistant to destruction by natural elements and can persist in the soil for more than one year after excretion by the cat. In the U.S.A., serological studies indicate that about 10–50% of the population has had contact with the parasite, the prevalence depending on the geographic locales and ethnic group [21]. In countries where eating lightly cooked or raw meat is more common, this figure can rise to as much as 85% (e.g., in France [7]). The incidence of disease in the developing fetus is, fortunately, not as high as these figures might at first suggest because it appears that the fetuses of women who are infected for a significant period of time prior to becoming pregnant are generally not at risk [21].

Diagnosis of congenital infection has in the past relied on serology (reviewed in [1,21]). This can be done postnatally or, ideally, pre-natally and relies on the relative titers of IgG and IgM (to deduce whether the titers are due to a current infection or legacy of a past infection). The factors contributing to the severity of disease in the developing fetus have been poorly understood. The only well-established factor is that the time of initial infection of the mother relative to conception is critical: infection significantly before conception such that an effective immune response has been mounted by the mother, results in little if any fetal disease. Infection immediately before or after conception (i.e., in the first trimester of pregnancy) results in severe disease for about 10–15% of fetuses [21].

In the past two decades, toxoplasmosis has dramatically increased in a relatively new group of patients who are in some way immunodeficient as a result of post-transplantation therapy [5, 9, 10, 22], neoplastic disease [11, 12, 13, 22] or, most recently, acquired immunodeficiency syndrome (AIDS) [3, 4, 5]. In such immunodeficient patients, the parasite can cause a disseminated, potentially fatal form of the disease [5, 22, 27].

Typical AIDS patients with toxoplasmosis exhibit signs referable to the central nervous system as the first symptom of the disease (reviewed in [22]), as one of the tissues most affected by the parasite is the brain, where massive numbers of parasites and of tissue cysts can be found. Infection is not limited to the brain, however, and parasites and tissue cysts can be found throughout the body [11]. The typical routine for diagnosis includes serology, computed tomography, magnetic resonance imaging and/or brain biopsy [1, 15, 16]. Of these, the only definitive route to diagnosis is the brain biopsy as this enables the direct visualization of the parasite, using immunoperoxidase staining [17].

In almost all AIDS patients and in most cases of toxoplasmosis in cancer patients and renal transplant recipients, toxoplasmosis results from a recrudescence of a previous latent (i.e., chronic) Toxoplasma infection. In contrast are patients at risk for the acute acquired infection, such as the fetus of a previously uninfected pregnant woman or a previously uninfected organ transplant recipient who receives an organ from a sero positive (i.e., Toxoplasma-infected) donor.

In general, there are three types of therapy: acute therapy, primary prophylaxis, and secondary prophylaxis. Acute therapy refers to treatment during an acute phase of an infection. In certain severely immunocompromised patient groups, this is followed by secondary prophylaxis (also known as maintenance therapy), which may be given over the entire life of a patient. Primary prophylaxis refers to treatment given to prevent the infection from occurring. Primary prophylaxis is often used in heart transplant recipients who are seronegative and who receive a heart from a seropositive donor. Primary prophylaxis is also used in pregnant women to prevent transmission from the mother to the fetus; that is, treatment is intended to prevent the mother who acquired the acute infection during pregnancy from passing the parasite to her fetus, as well as to treat the fetus in utero. Primary prophylaxis is also frequently used in AIDS patients to prevent activation of their latent (chronic) toxoplasma infections.

The course of treatment for toxoplasmosis in pregnant individuals is determined by the stage in pregnancy and whether the infection is acute or chronic. The purpose of early treatment is to attempt to prevent transmission of the parasite to the fetus. However, the fetus may be treated by treating the mother during gestation. If infection is acute, the antibiotic spiramycin may be administered but is of unproven efficacy. More effective drugs such as pyrimethamine and sulfadiazine, especially when used in combination, are often used after the first trimester of pregnancy (pyrimethamine may be teratogenic) when the diagnosis of infection of the fetus has been established by prenatal diagnostic techniques. Otherwise this particular drug combination is generally not used during pregnancy because of the potential toxicity for the mother and for the developing ferns [21].

Treatment of toxoplasmosis in non-pregnant individuals is initiated and maintained with a drug regimen involving a combination of folate antagonists, such as pyrimethamine and sulfadiazine [1, 14]. If the disease is identified soon enough, treatment is reasonably effective in combatting the acute disease. However, due to poor tolerance of the drugs, especially of the sulfa compounds in AIDS patients, maintenance on the drug therapy is frequently not possible, and recrudescence of the infection is often observed (that is, the drug therapy reduces but does not eliminate the parasite infection).

Rifamycin compounds are macrocyclic antibiotics that have been shown to be useful in a number of selective therapeutic applications. For example rifampin has the following structure:

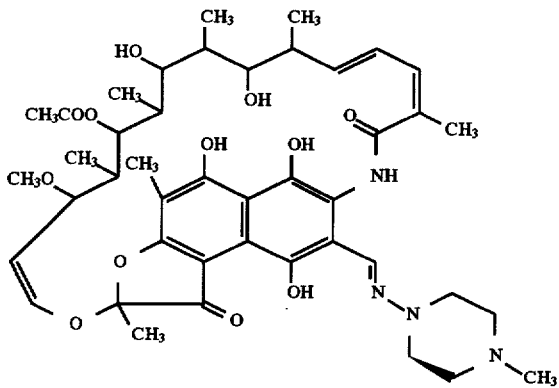

However, rifampin was tested for effectiveness in treating toxoplasmosis and was shown to have no protective effect in mice challenged with a lethal inoculum of toxoplasma [18]. Rifampin at concentrations of 50 µg/ml and greater significantly inhibited multiplication of toxoplasma in L-cell cultures. However, similar concentrations also inhibited growth of L-cells. Because the toxicity of rifampin for L-cells and its inhibition of Toxoplasma multiplication intracellularly in vitro occurred at the same concentration of the drug, it was reported [18] that rifampin was likely to inhibit Toxoplasma multiplication by its toxic effect on the L-cells. On the other hand, rifamycin compounds are generally considered to be effective against a limited number of pathological organisms, generally Gram-positive bacteria (including mycobacteria, staphylococci, and streptococci) and some Gram-negative bacteria (e.g., Brucella, Chlamydia, Haemophilus, Legionella, and Neisseria. spp); other Gram-negative bacteria (e.g., enterobacteria) are less sensitive, and spirochaetes and mycoplasma are known to be insensitive to treatment [19]. Individual compounds within the rifamycin series can be quite specific in their clinical indications. For example, the Physicians Desk Reference (1993 edition) lists only tuberculosis and asymptomatic infection with N. meningitidis as indications for treatment with rifadin. The related compound rifabutin, which is a spiropiperidyl rifamycin derivative, has also primarily been used in treating mycobacterial infections, notably tuberculosis [20]. More recently it has been used for primary prophylaxis of Mycobacterium avium-intracellulare infections in patients with AIDS [25]. However, these uses have been directed to bacteria, not protozoans which are members of the animal kingdom).

Accordingly, there remains a need for the development of therapeutic and prophylactic methods that can measurably add to the reliability of disease reduction in toxoplasmosis. By adding to the spectrum of drugs available for treating toxoplasmosis, problems arising from parasite resistance and side effects of existing medications can be overcome.

LITERATURE CITED.

1. McCabe, R. E. and Remington, J. S. (1983). Eur. J. Clin. Micro. 2: 95–104.
2. Dubey, J. P. and Beatty C. P. In Toxoplasmosis in animals and man. CRC Press, Boca Raton, Fla., U.S.A., pp. 1–220, 1988.
3. Gransden, W. R. and Brown, P. M. (1983). Brit. Med. J. 286: 6378.
4. Ensberger, W., Helm, E. B., Hopp, G., Stille, W. and Fischer, P.-.A. (1985). Deutsche Med. Wochenschrift 110: 83–86.
5. Luft, B. J., Brooks, R. G., Conley, F. K., McCabe, R. E. and Remington, J. S. (1984). JAMA 252: 913–917.
6. Feldman, H. A. (1965). Amer. J. Epidemiol. 81: 385–391.
7. Desmonts, G. and Couvreur, J. (1974). N. Engl. J. Med. 290: 1110–1116.
8. Remington, J. S. and Desmonts, G. (1976). In J. S. Remington and J. O. Klein (eds): Infectious Diseases of the Fetus and Newborn Infant. Philadelphia: Saunders, p. 191.
9. Peacock, J. E. J. r., Folds, J., Orringer, E., Luft, B. and Cohen, M. S. (1983). Arch. Intern. Med. 143: 1235–1237.
10. Cohen, S. N. (1970). J. Am. Med. Assn. 211: 657–660.
11. Gleason, T. H. and Hamlin, W. B. (1974). Arch. Intern. Med. 134: 1059–1062.
12. Vietzke, W. M., Gelderman, A. H., Grimley, P. M. and Valsamis, M. P. (1968). Cancer 21: 816–827.
13. Frenkel, J. K., Nelson, B. M. and Arias-Stella, J. (1975). Hum. Path. 6: 97–111.
14. Krahenbuhl, J. L. and Remington, J. S. (1982). In S. Cohen and K. S. Warren (eds): Immunology of Parasitic Infections. Oxford: Blackwell, pp. 356–421.
15. Cesbron, J. Y., Capron, A., Oviaque, G. and Santoro, F. (1985). J. Imm. Meth. 83: 151–158.
16. Erlich, H. A., Rodgers, G., Vaillancourt, P., Araujo, F. G. and Remington, J. S. (1983). Infect. Immun. 41: 683–690.
17. Conley, F. K., Jenkins, K. A. and Remington, J. S. (1981). Hum. Pathol. 12: 690–698.
18. Remington, J. S., Yagura, T., and Robinson, W. S. (1970). The effect of rifampin on Toxoplasma gondii. Proc. Soc. Exp. Biol. and Med. 135: 167–172.
19. Singleton, P., and Sainsbury, D., eds. (1987). Dictionary of Microbiology and Molecular Biology, Second Edition, Antony Rowe, Ltd., Chippenham (England).
20. Woodley, C. L., and Kilburn, J. O. (1982). Am. Rev. Respir. Dis. 126: 586–587.
21. Remington, J. S. and Desmonts, G. (1990). Toxoplasmosis. In Infectious Diseases of the Ferns and Newborn Infant, Third Edition, J. S. Remington, J. O. Klein, eds. Philadelphia: W. B. Saunders Company, pp. 89–195.
22. Israelski, D. M. and Remington, J. S.: AIDS-associated toxoplasmosis. In The Medical Management of AIDS, Third Edition, M. A. Sande, and P. A. Volberding, eds. Philadelphia: W. B. Saunders Company, pp. 319–345, 1992.
23. McLeod, R., and Remington, J. S. (1992). Toxoplasmosis. In Nelson Textbook of Pediatrics, Fourteenth Edition. R. E. Behrman, R. M. Kliegman, W. E. Nelson and V. C. Vaughan, eds. Philadelphia: The W. B. Saunders Company, pp. 883–892.
24. McLeod, R. and Remington, J. S. (1987). Toxoplasmosis. In Harrison's Principles of Internal Medicine, Eleventh Edition, E. Braunwald, K. J. Isselbacher, R. G. Petersdorf, J. D. Wilson, J. B. Martin and A. S. Fauci, eds. New York: McGraw-Hill Book Company, pp. 791–797.
25. Hoy, J., Mijch, A., Sandland, M. Grayson, L. Lucas, R., and Dwyer, B. (1990). Quadruple-Drug Therapy for Microbacterium Avium-Intracellular Bacteremia in AIDS patients. J. Infect. Dis. 161:801–805.
26. Araujo, F. G., Lin, T., and Remington, J. S. (1993). The Activity of Atovaquone (566C80) in Murine Toxoplasmosis is Markedly Augmented when Used in Combination with Pyrimethamine or Sulfadiazine, J. Infect. Dis. 167:494–497.

27. Ruskin, J. and Remington, J. S. (1976). Toxoplasmosis in the Compromised Host. Ann. Intern. Med., 84:193–199, 1976.

28. Araujo, F. G. (1992). Depletion of CD4+ T cells but not inhibition of the protective activity of IFN-γ prevents cure of toxoplasmosis mediated by drug therapy in mice. J. Immunol. 149:3003–3007.

29. Araujo, F. G., R. M. Shepard, and J. S. Remington (1991). In vivo activity of the macrolide antibiotics azithromycin, roxithromycin and spiramycin against *Toxoplasma gondii*. Eur. J. Clin. Microbiol. Infect. Dis. 10:519–524.

30. Araujo, F. G., J. Huskinson-Mark, W. E. Gutteridge, J. S. Remington (1992). In vitro and in vivo activities of the hydroxynaphthoquinone 566C80 against the cyst form of *Toxoplasma gondii*. Antimicrob. Agents Chemother. 36:326–330.

31. Araujo, F. G., J. Huskinson, and J. S. Remington (1991). Remarkable in vitro and in vivo activities of the hydroxynaphthoquinone 566C80 against tachyzoites and cysts of *Toxoplasma gondii*. Antimicrob. Agents and Chemother. 35:293–299.

32. Araujo, F. G., P. Prokocimer, and J. S. Remington (1992). Clarithromycin-minocycline is synergistic in a murine model of toxoplasmosis. J. Infect. Dis. 165:788.

33. Chiodini, R. J., J. M. Kreeger, and W. R. Thayer (1993). Use of rifabutin in treatment of systemic *Mycobacterium paratuberculosis* infection in mice. Antimicrob. Agents Chemother. 37:1645–1648.

34. Dannemann, B., J. A. McCutcham, D. M. Israelski, D. Antoniskis, C. Leport, B. Luft, J. Nussbaum, N. Clumeck, P. Morlat, J. Chiu, J.-L. Vilde, M. Orellana, D. Feigal, A. Bartok, P. Halsetin, J. Leedom, J. S. Remington and the California Collaborative Treatment Group (1992). Treatment of toxoplasmic encephalitis in patients with Acquired Immunodeficiency Syndrome: A randomized trial comparing pyrimethamine plus clindamycin to pyrimethamine plus sulfadiazine. Ann. Intern. Med. 116:33–43.

35. Dannemann, B. R., D. M. Israelski, and J. S. Remington (1988). Treatment of toxoplasmic encephalitis with intravenous clindamycin. Arch. Intern. Med. 148:2477–2482.

36. Ellner, J. J., M. J. Goldberger, and D. M. Parenti (1991). *Mycobacterium avium* infection in AIDS: a therapeutic dilemma in rapid evolution. J Infect Dis, 163:1326–1335.

37. Heifets, L. B., M. D. Iseman, and P. J. Lindholm-Levy. Bacteriostatic and bactericidal effects of rifabutin (ansamycin, LM 427) on *Mycobacterium avium* clinical isolates, p. 180–183. In M. Casal (ed.) Mycobacteria of Clinical Interest 1986. Amsterdam: Elsevier Science.

38. Horsburgh, C. R. (1991). *Mycobacterium avium* complex infections in the acquired immunodeficiency syndrome. N. Engl. J. Med. 324:1332–1338.

39. Hughes, W. T., W. Kennedy, J. Shenep, P. M. Flynn, S. V. Hetherington, G. Fullen, D. J. Lancaster, D. S. Stein, S. Palte, D. Rosenbaum, S. H. T. Liao, M. R. Blum, M. D. Rogers (1991). Safety and pharmacokinetics of 566C80, a hydroxynaphthoquinone with anti-*Pneumocystis carinii* activity: A phase I study in human immunodeficiency virus (HIV)-infected men. J. Infect. Dis. 163:843–848.

40. Israelski, D. M., B. R. Dannemann, and J. S. Remington. Toxoplasmosis in patients with AIDS, p. 241–264. In M. A. Sande, and P. A. Volberding (eds.) The medical management of AIDS-1990. Philadelphia: W. B. Sounders.

41. Israelski, D. M., F. G. Araujo, F. K. Conley, Y. Suzuki, S. D. Sharma, J. S. Remington (1989). Treatment with anti-L3T4 (CD4) monoclonal antibody reduces the inflammatory response in toxoplasmic encephalitis. J. Immunol. 142:954–958.

42. Narang, P. K., R. C. Lewis, and J. R. Bianchine (1992). Rifabutin absorption in humans: Relative bioavailability and food effect. Clin. Pharmac. Therap. 52:335–341.

43. McCabe, R. E. and J. S. Remington. *Toxoplasma gondii*, p. 2090–2103. In Third ed. Principles and Practice of Infectious Diseases-1990. G. L. Mandell, J. Dauglas R. G., and J. E. Bennett (eds.) London: Churchill Livingstone, Inc.

44. Hunter, C. A., J. S. Abrams, M. H. Beaman, and J. S. Remington (1993). Cytokine mRNA in the central nervous system of SCID mice infected with *Toxoplasma gondii*: importance of T-cell independent regulation of resistance to *T. gondii*. Infect. Immun. 61:4038–4044.

SUMMARY OF THE INVENTION

Accordingly, it is an object of the invention to provide a class of compounds effective in protecting an infected or potentially infected host mammal against toxoplasmosis.

It is a further object of invention to provide such a class of compounds with a minimum number of side effects.

It is a still further object of the invention to provide a composition effective in vivo in preventing the lethal effects of toxoplasmosis or otherwise reducing the severity of the disease, preferably with a class of compounds of proven clinical tolerance for other indications.

These and other objects of the invention, as will hereafter become more readily apparent, have been accomplished by providing a method of reducing the severity of toxoplasmosis resulting from infection of a mammalian host with *Toxoplasma gondii*, which comprises administering to a mammalian host in need of such treatment, either after infection or before exposure to such infection, a therapeutically effective amount of a compound that is a spiropiperidyl derivative of rifamycin S, wherein the derivative comprises an imidazole ring that includes carbons at positions 3 and 4 of the rifamycin ring, the carbon at position 2 of the imidazole ring also being a ring carbon at position 4 of a piperidine ring system, thereby forming a spiropiperidyl ring system, the spiropiperidyl ring system optionally comprising a lower hydrocarbon substituent on the nitrogen of the piperidine.

BRIEF DESCRIPTION OF THE DRAWINGS

The invention now being generally described, the same will be better understood by reference to the following detailed description of specific embodiments when considered in combination with the figures that form part of the specification, wherein:

FIG. 1A is a graph showing survival of mice infected with *T. gondii* and treated with various concentrations of rifabutin (RIF).

FIG. 1B is a graph showing survival of mice following infection with cysts of the C56 strain of *T. gondii* and treated with various concentrations of rifabutin (RIF).

FIG. 4 is a graph showing survival of mice infected with *T. gondii* and treated with high concentrations of rifabutin alone or in combination with sulfadiazine.

FIG. 5 is a graph showing survival of mice infected with *T. gondii* and treated with rifabutin (RIF) alone or in combination with pyrimethamine (PYR).

FIGS. 7A and 7B depict survival of mice infected with *T. gondii* and treated with rifabutin (RIF) alone or in combination with atovaquone (ATO).

FIG. 8 is a graph showing survival of mice infected with *T. gondii* and treated with rifabutin (RIF) alone or in combination with azithromycin (AZITHRO).

DESCRIPTION OF SPECIFIC EMBODIMENTS

Figure 2:
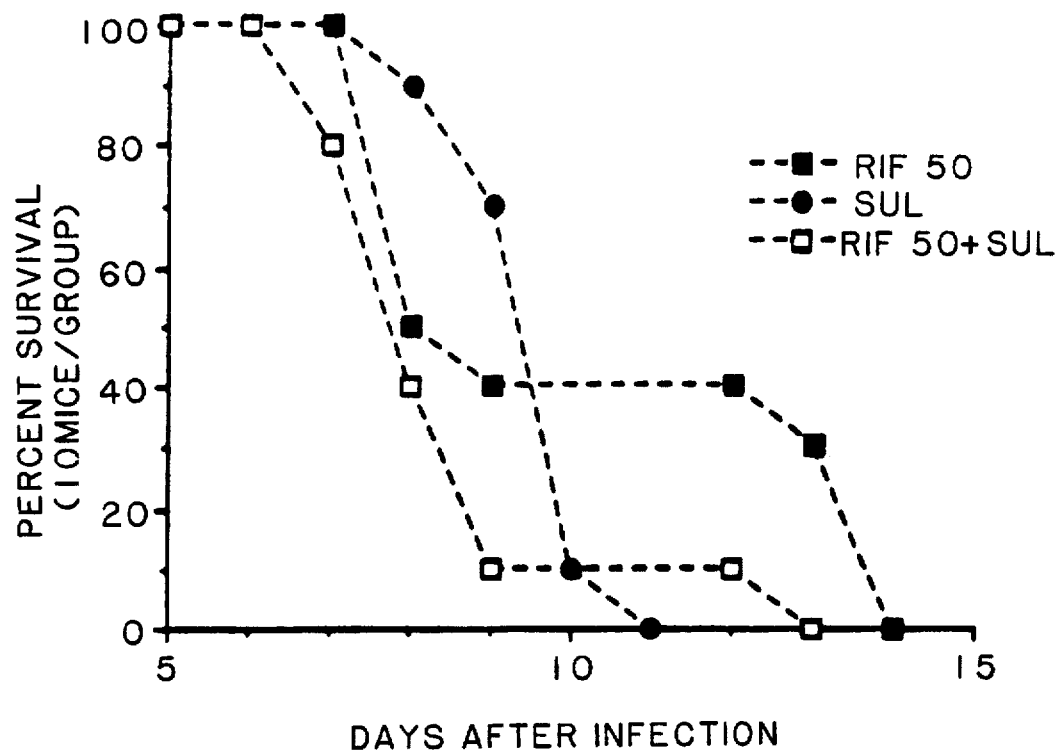
FIG. 2 is a graph showing survival of mice infected with *T. gondii* and treated with low concentrations of rifabutin (RIF) alone or in combination with sulfadiazine (SUL).

The present inventors have discovered that spiropiperidyl derivatives of rifamycin S are surprisingly effective in protecting a mammalian host against infection by the disease-causing organism associated with toxoplasmosis. This discovery contrasts with previously available information on the effectiveness of rifamycin compounds, such as rifampin, which was previously shown to be ineffective in protecting against toxoplasmosis. This remit is particularly surprising in view of the relatively close structure of the ineffective rifampin compound and the spiropiperidyl derivatives of rifamycin S that are now shown to be effective.

Compounds of the invention are semi-synthetic derivatives of rifamycin S comprising a fused imidazole ring that includes carbons at positions 3 and 4 of the rifamycin ring, the carbon at position 2 of the imidazole ring also being a ring carbon at position 4 of a piperidine ring system, thereby forming a spiropiperidyl ring system. The nitrogen atom of the piperidine ring is optionally substituted with a lower hydrocarbon substituent, typically containing from 1 to 8 (preferably 3-5) carbons, usually branched, and most preferably being an iso-butyl group. However, other hydrocarbon groups can be present at this location, such as methyl, ethyl, propyl, isopropyl, butyl, sec-butyl, tert-butyl, pentyl, iso-pentyl, hexyl, and iso-hexyl. Unsaturated analogues of these saturated alkyl groups (especially alkenes, particularly those in which the double bond (or bonds) is located so that an $sp^3$ hybridized carbon is attached to the nitrogen atom of the piperidine ring) are also permitted.

Accordingly, the compounds used in the practice of the invention will typically have the formula:

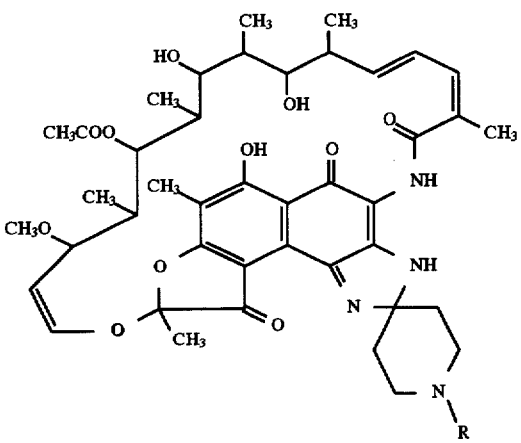

in which R represents one of the indicated alkyl groups.

These compounds do not represent a new class of compounds but rather are compounds that have been previously known for other uses. The spiropiperidyl derivatives of rifamycin S are semi-synthetic molecules produced by modification of natural rifamycins produced by *Nocardia mediterranei* (also known as *Streptomyces mediterranei*). Mixtures of rifamycins A–E are generally produced in culture, but the proportion of the desired intermediate rifamycin B can be increased by the addition of sodium diethyl barbiturate in the growth medium. Rifamycin B is only an intermediate, since an aqueous oxygenated solutions spontaneously gives rise to other rifamycins, such as O and S. Rifamycin S is the starting point for the production of a number of semi-synthetic rifamycins. These include the specific compound known by the name rifamycin (also referred to as rifamycin SV), which is obtained by mild reduction of rifamycin S. Other derivatives produced by modification of rifamycin S include rifamide and rifampicin (also called rifampin), the latter having a structure as shown in the background section above. Total synthesis of rifamycin S has also been reported. See, for example, H. Nagaoka, et al., J Am. Chem. Soc. 102:7962 (1980); H. Iio, et al., ibid. 7965; H. Nagaoka and Y. Kishi, Tetrahedron, 37:3873 (1981). For a review of chemistry of rifamycins, see K. L. Reinhart, et al., Fortschr. Chem. Org. Naturst. 33:231–307 (1976). Synthesis of spiropiperidyl rifamycins is described in L. Marsili, et al., J. Antibiot. 34:1033–1038 (1981). Spiropiperidyl rifamycin compounds and their activity as antibacterials against Gram-positive and Gram-negative bacteria, including *Microbacterium tuberculosis*, are described in U.S. Pat. No. 4,219,478. Also see related U.S. Pat. Nos. 4,086,225, and 4,327,096. As an example of the systematic chemical nomenclature of compounds of the invention, rifabutin is (9S,12E,14S,15R,16S,17R,18R,19R, 20S ,21S ,22E,24Z)-6,16,18,20-tetrahydroxy-1'-isobutyl-14-methoxy-7,9,15,17,19,21,25-heptamethyl-spiro[9,4-(epoxypentadeca[1,11,13]trienimino)-2H-furo[2',3',7,8] naphth[1,2-d]imidazole-2,4'-piperidine]-5,10,26-(3H,9H)-trione-16-acetate.

Compounds of the invention method are soluble in chloroform and methanol, sparingly soluble in ethanol, and slightly soluble in water. The compounds can be prepared in standard pharmaceutical compositions of the same type used for other rifamycin compounds. A composition for use in vivo generally will contain a pharmaceutically acceptable carrier. By this is intended either solid or liquid material, which may be inorganic or organic and of synthetic or natural origin, with which the active component of the composition is mixed or formulated to facilitate administration to a subject. Any other materials customarily employed in formulating pharmaceutical are suitable. Solid carriers include natural and synthetic cloisonne silicates, for example natural silicates such as diatomaceous earths; magnesium silicates, for example talcs; magnesium aluminum silicates, for example attapulgites and vermiculites; aluminum silicates, for example kaolinites, montmorillonites, and micas; calcium carbonate; calcium sulfate; synthetic hydrated silicone oxides and synthetic calcium or aluminum silicates; elements such as carbon or sulfur; natural and synthetic resins such as polyvinyl alcohol; and waxes such as paraffin and beeswax. Examples of suitable liquid carriers include water and aqueous solutions containing oxygenated organic compounds such as ethanol. Buffers and other materials normally present in pharmaceutical preparations, such as flavoring and suspending agents, can also be present. Pharmaceutical carriers differ from typical solutions and suspensions in that they are specifically prepared for use in vivo to exclude substances that may be harmful to the host to whom the composition is administered (e.g., removal of bacterial toxins).

As an example of a pharmaceutical composition, rifabutin can be present at 150 mg per capsule in a gelatin capsule intended for oral administration. The remainder of the capsule will contain, for example, as inactive ingredients, microcrystalline cellulose, magnesium stearate, red iron oxide, silica gel, sodium lauryl sulfate, titanium dioxide, and edible white ink.

Compositions containing spiropiperidyl rifamycins have been indicated for other pharmaceutical uses, such as antimycobacterial indications, including tuberculosis. The clinical pharmacology of these compounds is thus known. For example, following a single oral admission of 300 mg of rifabutin in normal subjects, rifabutin is readily absorbed from the gastrointestinal tract with mean (±SD) peak plasma levels ($C_{max}$) of 375 (±267) mg/mL (range: 141 to 1033 mg/mL) attained in 3.3 (±0.9) hours ($T_{max}$ range: two to four hours). Plasma concentrations post-$C_{max}$ decline in an apparent bi-phasic manner. Kinetic dose-proportionality has been shown in healthy normal volunteers and in early symptomatic Human Immunodeficiency Virus (HIV) positive patients at doses from 300 mg to 900 mg. Rifabutin is eliminated slowly from plasma in the same manner as other rifamycin compounds.

As indicated previously, the specific method of the present invention is directed to the treatment and/or prophylaxis of toxoplasmosis. For treatment, the dosage on the first day (referred to as a loading dose) is often but not necessarily higher than on succeeding days. A typical loading dose would be 0.25–400 mg/kg/day (preferably 1–200, more preferably 2–200), with typical treatment dosages at half these values. These doses are in the range of normal doses for other rifamycin compounds. For prophylactic use, doses in the lower half of the normal range are used, generally without a loading dose.

In a typical treatment regimen, spiropiperidyl rifamycins can be administered to humans as a single dose of about 300 mg per os ("po"; orally) once a day, generally at breakfast, or, if not tolerated in a single dose, can be divided into two doses of about 150 mg each with morning and evening meals. The half-life in serum of rifabutin is 16 hours. The drug is eliminated in part by the kidneys, with urine concentrations being about 100-fold higher than those in the plasma. The drug also appears in the bile at a concentration similar to that in the urine. The drug is taken up by all tissues and is especially concentrated in lungs, where levels reach 5–10 times higher than those in plasma. For a study of the clinical effects of rifabutin, see R. J. O'Brien et al., Reviews of Infectious Diseases, 9:519–530 (1987).

Subjects to be treated include those acutely infected with *Toxoplasma gondii* and, for prophylactic use, those subjects who may in the future be exposed to the disease-causing organism or immunosuppressed patients with chronic toxoplasma infection to prevent recrudescence or relapse of the infection. In view of the widespread occurrence of the organism, this can include all immunocompromised individuals. Selection of a particular dose and determination of the timing of dosages is best left to the decision of a physician or veterinarian in the same manner as for other treatments with rifamycin compounds, so that the dosage can be raised or lowered as necessary. Although the method is intended for use in humans in part, veterinary use is also contemplated, particularly in domesticated mammals (such as sheep, pigs, and cats) that are also known hosts for *T. gondii*.

A particularly interesting aspect of the spiropiperidyl rifamycin compounds is their ability to act synergistically with sulfonamides. Sulfonamides comprise a well known group of antimicrobial agents that are mostly derivatives of sulfanilamide (p-aminobenzenesulfonamide). They halt or retard the growth of a wide range of Gram-positive and Gram-negative bacteria, as well as various protozoa (such as coccidia and Plasmodium spp). Sulfanilamides are often used in combination with other chemotherapeutic agents for treating urinary tract infections and various intestinal disorders.

Organisms which synthesize their own folic acid and which cannot use an exogenous supply of the vitamin are sensitive to sulfonamides provided that the cells are permeable to the drug. This is a result of the ability of sulfonamides to act as structural analogs of p-aminobenzoic acids (PABA). Sulfonamides competitively inhibit the incorporation of PABA during folic acid synthesis. Thus, the combinations in which they are most often used involve other folic acid antagonists. Organisms which require exogenous folic acid for growth are insensitive to sulfonamide treatment.

There are many sulfonamide drugs that differ in their clinical properties and toxicities. Most are derivatives bearing substituents at the nitrogen of the sulfonamide group (i.e., $NH_2C_6H_4SO_2NHR$, where R represents the substituent). Substitution at the p-amino group normally results in loss of antibacterial activity. However, such derivatives are often hydrolyzed in vivo to an active form and can therefore be administered in inactive form. For example, p-N-succinylsulfathiazole and phthalylsulfathiazole are inactive but are hydrolyzed in the lower intestine to release the active component sulfathiazole.

A number of active sulfonamides include, e.g., sulfacetamide (N-[4-aminophenyl)sulfonyl]-acetamide); sulfadiazine; sulfadimethoxine (4-amino-N-(2,6-dimethoxy-4-pyrimidinyl)benzenesulfonamide); sulfadimidine (sulfamethazine: 4-amino-N-(4,6-dimethyl-2-pyrimidinyl) benzenesulfonamide); sulfaguanidine (4-amino-N-(aminoiminomethyl)benzenesulfonamide); sulfamethoxazole (4-amino-N-(5-methyl-1,3,4-thiadiazol-2-yl) benzenesulfonamide); sulfamethoxazole (4-imino-N-(5-methyl-3-isoxazolyl)benzenenesulfonamide); sulfathiazole (4-azino-N-2-thiaamide); and sulfathiazole (4-amino-N-2-thiazolylbenzenesulfonamide).

The present inventors have discovered that in addition to the spiropiperidyl rifamycin compounds' synergistic interaction with sulfonamides, the spiropiperidyl rifamycin compounds also act synergistically as demonstrated herein with a number of antimicrobial compounds in the treatment of toxoplasmosis, including the antibacterials clindamycin, clarithromycin, and azithromycin; the anti-malarial drug pyrimethamine; and atovaquone. These synergistic interactions provide a further advantage within the general scope of the invention (treatment with spiropiperidyl rifamycins, whether or not in combination with other drugs) by providing certain synergistic effects when spiropiperidyl rifamycins are used in combination with selected other classes of drugs.

Accordingly, one embodiment of the invention is the use of spiropiperidyl rifamycin compounds in combination with lincosamides to achieve a synergistic effect. Lincosamides comprise a well known group of antimicrobial agents that contain lincosamine (i.e., 6-amino-6,8-dideoxyoctose). They halt or retard the growth of a range of Gram-positive and Gram-negative bacteria. There are many lincosamide drugs that differ in their clinical properties and toxicities. Any lincosamide can be used in combination with rifabutin or other spiropiperidyl rifamycin compounds in the treatment or prevention of toxoplasmosis; preferred are those that further act synergistically as taught herein. Active lincosamides include lincomycin, its semisynthetic derivative clindamycin (7-chloro-7-deoxylincomycin), and celesticetin. Other useful lincosamide derivatives include those that can be hydrolyzed in vivo to an active form and can therefore be administered in inactive form. For example, clindamycin palmitate HCl is inactive in vitro, but rapid in vivo hydrolysis converts it to antibacterially active clindamycin. Clindamycin phosphate, a water soluble ester of clindamycin and phosphoric acid, is another preferred lincomycin derivative.

A number of individual compounds and class of compounds act synergistically with spiropiperidyl rifamycin compounds. For example, spiropiperidyl rifamycin compounds act synergistically with pyrimethamine. Pyrimethamine is a folic acid antagonist effective against protozoans. Spiropiperidyl rifamycin compounds also act synergistically with hydroxynaphthoquinones. A preferred hydroxynaphthoquinone is atovaquone. Other preferred hydroxynapththoquinone antibiotics are those that have activity against *T. gondii* when used alone. Spiropiperidyl rifamycin compounds act synergistically with azalides. Preferred azalides are azithromycin and its derivatives. Other preferred azalide antibiotics are those that have activity against *T. gondii* when used alone. Spiropiperidyl rifamycin compounds further act synergistically with macrolide antibiotics. Preferred macrolides are clarithromycin and its derivatives. Other preferred macrolide antibiotics are those that have activity against *T. gondii* when used alone. Such preferred macrolides include roxithromycin and spiramycin. Macrolides of the invention also include angolamycin, carbomycin, chalcomycin, cirramucin, erythromycin, lankomycin, leucomycin, megalomycin, methymycin, narbomycin, niddamycin, oleandomycin, relomycin, troleandomycin, tylosin, polyene antibiotics, and their active derivatives.

These and the other antimicrobial agents discussed herein may be natural (produced from natural or genetically engineered sources), semi-synthetic or wholly synthetic. As these are all known compounds, descriptions of synthesis can be found in the published scientific literature.

In one aspect of the invention, these drugs are used in combination with rifabutin or other spiropiperidyl rifamycin compounds as pharmaceuticals or to produce medicaments useful in the treatment or prevention of toxoplasmosis infection or toxoplasmosic encephalitis ("TE"). A pharmaceutical would comprise a therapeutically effective amount of rifabutin or other spiropiperidyl rifamycin compound in combination with a therapeutically effective amount of one or more of the drugs discussed herein as synergistically effective against toxoplasma. Alternatively, these drugs can be used individually to produce medicaments that are then used in combination with rifabutin or other spiropiperidyl rifamycin compounds to treat or prevent toxoplasmosis infection or TE. Combination medicaments or treatments comprise rifabutin or other spiropiperidyl rifamycin compounds with at least one other anti-toxoplasma compound as taught herein. Pharmaceutical carriers, dosages, routes of administration, and treatment regimens are as previously discussed herein, although they can be effectively modified by a clinician, using as a guideline the dosages presented herein and dosages previously known for use in treatment of toxoplasmosis. Of course, because of the synergistic activity discovered herein, lower dosages than those previously reported are now available to the clinician or veterinarian.

In addition to their synergistic interaction with the above compounds, the spiropiperidyl rifamycin compounds should also act synergistically with a number of antibiotic compounds in the treatment of toxoplasmosis including antiviral such as gamma interferon, compounds effective against *T. gondii* such as macrolides roxithromycin and spiramycin and tetracylines, e.g. minocycline, and their congeners, and other compounds effective against other protozoan-caused diseases.

One specific aspect of the invention within the scope of treating "toxoplasmosis" is a method of reducing the severity of toxoplasmosic encephalitis resulting from infection of a mammalian host with *Toxoplasma gondii*. TE can be reduced in severity by administering to a host in need of treatment, either after infection or before exposure to a *T. gondii* infection, a therapeutically effective amount of a compound that is a spiropiperidyl derivative of rifamycin S, wherein the derivative includes an imidazole ring that includes carbons at positions 3 and 4 of the rifamycin ring, the carbon at position 2 of the imidazole ring also being a ring carbon at position 4 of a piperidine ring system, thereby forming a spiropiperidyl ring system, the spiropiperidyl ring system optionally including a lower hydrocarbon substituent on the nitrogen of the piperidine. A preferred compound for treatment is rifabutin. Pharmaceutical carriers, dosages, routes of administration, and treatment regimens are as previously discussed herein for treatment of toxoplasmosis. In a further aspect of the invention, TE can be reduced in severity by administering a therapeutically effective amount of a combination of a spiropiperidyl rifamycin compound with a drug discussed herein that enhances the effectiveness a spiropiperidyl rifamycin compound for treatment or prevention of toxoplasmosis. Pharmaceutical carriers, dosages, routes of administration, and treatment regimens are as previously discussed herein for combination drug treatment of toxoplasmosis.

As provided herein, and as demonstrated by the following Examples, spiropiperidyl rifamycin derivatives, particularly rifabutin, are effective in the protection of a mammalian host, including an immunocompromised host, against infection with *Toxoplasma gondii*. The compounds also demonstrate a synergistic effect in combination with other drugs, particularly with sulfonamides, and provide full protection in this model study against toxoplasmosis. The in vivo results with rifabutin presented in Example 1, which demonstrate that rifabutin alone is effective in the treatment of toxoplasma related diseases, contrast with and are unexpected in light of results obtained with rifampin [18].

Demonstrated herein is that rifabutin alone is effective in the treatment of toxoplasma related diseases, and further that rifabutin acts synergistically in combination with other drugs. This adds significantly to the spectrum of drugs available for treating toxoplasmosis, thereby overcoming problems arising from parasite resistance and side effects of existing medications. In addition, rifabutin was found to decrease the inflammatory response associated with toxoplasmic encephalitis (Example 8). Accordingly, the results presented herein provide for therapeutic and prophylactic methods that measurably add to the reliability of disease reduction in toxoplasma infections.

The anti-*T. gondii* effect in mice with disseminated acute toxoplasmosis due to infection with RH tachyzoites was enhanced significantly when rifabutin was used in combination with pyrimethamine, sulfadiazine, clindamycin, or atovaquone, as demonstrated in the Examples. These drugs are preferred since they are either presently in use or are undergoing clinical trials for treatment of toxoplasmosis. Azithromycin or clarithromycin in combination with rifabutin were also demonstrated in the Examples as enhancing the anti-*T. gondii* effect. The present invention allows for effectively treating toxoplasmosis and toxoplasmic encephalitis in severely immunocompromised patients. As demonstrated herein, the combination of ineffective doses of rifabutin and clindamycin resulted in remarkable and significant protection of mice with disseminated acute toxoplasmosis (Example 4) and in *T. gondii*-infected immunocompromised mice (Example 9). Clindamycin is currently most frequently used as an alternative to sulfonamides when side-effects develop during treatment with the pyrimethamine-sulfonamide combination [34, 35]. Furthermore, although pyrimethamine and sulfonamides may be responsible for inconvenient side effects, particularly in AIDS patients, the combinations taught herein allow for significant reduction in their dosing to minimize or eliminate their untoward side effects. The combination of rifabutin-atovaquone was demonstrated as effective against toxoplasmosis (Example 5). Atovaquone is active both against *T. gondii* [31, 32] and *Pneumocystis carinii* [39]. Rifabutin, on the other hand, is active against mycobacteria and is now being used for treatment and prophylaxis of organisms of the *Mycobacterium avium* complex [36]. Thus, the results with the combination rifabutin-atovaquone indicate use of this combination for treatment and prophylaxis of the three of the most frequently encountered opportunistic agents in AIDS patients.

The invention now being fully described, the following examples are provided for illustration only and are not intended to limiting of the invention unless so stated.

EXAMPLES

Example 1

Activity of rifabutin against *T. gondii* in murine model of acute toxoplasmosis An experiment was carried out to determine the in vivo protective activity of rifabutin against toxoplasmosis. The model used was a mouse model using Swiss Webster female mice weighing approximately 20 grams at the time of the experiment. The rifabutin used in the experiment was obtained commercially from Adria as a pharmacologically pure compound and was solubilized in phosphate buffered saline, pH 7.2, and then sonicated for four pulses of one minute each. The experiment was carried out on four groups of mice (3 experimental and one control) with 10 mice per group. The mice were infected with *T. gondii* tachyzoites of the RH strain obtained from the peritoneal fluid of carrier mice according to published standard procedures for this model [26]. The peritoneal fluid was collected into Earle's balanced salt solution containing 10% fetal calf serum and 10 units of heparin/ml. The preparation was then filtered through glass wool, centrifuged at 500×g for 5 minutes at 4° C., and the sediment was resuspended and forced through a 27-gauge needle. The organisms were quantified by counting on a Neubauer-Levy hemacytometer, and appropriate dilutions in Eagle's minimum essential medium (MEM) were made. The lethal inoculum of the RH strain of *T. gondii* is approximately one tachyzoite. Mice infected with our RH strain never survive with any living parasites. Thus, survivors in our studies had the organism eradicated by the therapy. Mice were infected with an intraperitoneal dose of $2.5 \times 10^3$ tachyzoites of the RH strain (a dose that normally results in death of 100% of normal mice by day 8 or 9). Beginning 24 hours after ip infection, one group of mice was treated with 50 mg/kg/day of rifabutin, a second with 100 mg/kg/day, and a third with 200 mg/kg/day administered orally by gavage for a period of ten days. Thereafter, mice were followed for an additional 20 days and the date of death noted. Mice dying during the experiment were examined for the presence of *T. gondii* in their peritoneal fluid for verification of the cause of death.

As shown in FIG. 1A, significant protection was noted in mice treated with doses of rifabutin of 100 mg/kg/day and higher. Administration of 200 mg/kg/day resulted in survival of 9 out of the 10 mice in that group for the entire 30-day test period. In the 100 mg/kg/day group, six mice were still alive 15 days after infection, while two survived the 30-day observation period. In contrast, all 10 of the control mice died within the expected 9-day period, and only 4 mice survived beyond 10 days in the 50 mg/kg/day group, with all of the latter dying within 14 days. Thus, the dose of 50 mg/kg/day resulted in significant prolongation of time to death as compared with untreated controls even though all of the mice eventually died. One hundred percent of mice infected ip with tachyzoites of the RH strain survived when treated with doses of 300 or 400 mg/kg/day rifabutin. Identical results were obtained when rifabutin was prepared by dissolution in phosphate buffered saline, pH 6.8, followed by sonication for 30 seconds.

Activity of different doses of rifabutin (RIF) in disseminated acute murine toxoplasmosis following ip infection with cysts of the C56 strain of *T. gondii* was also examined. Adult, outbred Swiss-Webster (SW), females, weighing 20 g at the beginning of each experiment were used [26, 29, 30, 31]. Treatment was initiated 3 days after infection. Treatment was for 10 days. Rifabutin was prepared by dissolution in phosphate buffered saline, pH 6.8, followed by sonication for 30 seconds. As shown in FIG. 1B, significant protection was obtained for mice treated with doses of rifabutin of 100 mg/kg/day and higher. Administration of 200 mg/kg/day resulted in survival of 9 out of the 10 mice in that group for the entire 30-day test period. Administration of 300 mg/kg/day resulted in survival of 10 out of the 10 mice in that group for the entire 30-day test period. In the 100 mg/kg/day group, six mice were still alive 15 days after infection, while two survived the 30-day observation period. All 10 of the control mice died within the expected 9-day period, while 4 mice survived beyond 10 days in the 50 mg/kg/day group, with all of the latter dying within 14 days. Ten of 10 infected mice survived for the entire test period when treated with 300 mg/kg/day.

The above results indicate significant activity for rifabutin in treatment of disseminated acute murine toxoplasmosis caused by different strains of *T. gondii*. A dose of 200 mg/kg/day administered for 10 days protected at least 80% of the mice against death due to infection either with tachyzoites of the RH strain or with cysts of the C56 strain. Doses of 300 or 400 mg/kg/day protected 100% of the mice and apparently were not toxic for the animals since non-infected mice treated with these doses did not show any clinical signs of toxicity and did not lose weight. Although pharmacokinetic studies were not conducted in the present investigation, in normal human volunteers [42] rifabutin is rapidly but incompletely absorbed from the gastrointestinal tract. The average terminal half-life in humans after oral administration was 36 hours and the bioavailability was 84.8% [42].

RH tachyzoites and C56 cysts were used in these experiments because of previous reports that demonstrated variation in susceptibility of different strains of *T. gondii* to different drugs [29]. In addition, the pathogenesis of the infection produced by inoculation of tachyzoites or cysts differ. Ip inoculation of RH tachyzoites results in a fulminant infection with large numbers of tachyzoites being produced in the peritoneal cavity. One hundred percent mortality usually occurs within 5 to 8 days after infection with an inoculum as small as $10^2$ organisms. In contrast, oral inoculation of cysts of the C56 strain results in an infection which progresses slower. Depending on the inoculum size, mortality does not occur until approximately 15 days of infection.

Example 2

In vivo activity of rifabutin in combination with a sulfonamide against *T. gondii* in a murine model of acute toxoplasmosis An experiment was carried out in the manner described for Example 1, but with the additional administration of a sulfonamide. Conditions were as described in the first example except for the following changes. Seven groups of mice (10 mice per group) were infected by intraperitoneal injection of $2.5 \times 10^3$ tachyzoites of *T. gondii* and then given oral treatment by gavage with rifabutin beginning 24 hours after infection and continuing for 10 days. Sulfadiazine, sodium salt, was obtained from Sigma Chemical Co. or City Chem. Corp., New York, N.Y., and was administered ad libitum during the entire period of treatment in the drinking water at a concentration of 80 mg/liter to some groups as follows:

Group 1—Rifabutin alone, 50 mg/kg/day.

Group 2—Rifabutin alone, 100 mg/kg/day.

Group 3—Rifabutin alone, 200 mg/kg/day.

Group 4—Sulfadiazine alone at 80 mg/L.

Group 5—Rifabutin, 50 mg/kg/day, plus sulfadiazine at 80 mg/L.

Group 6—Rifabutin, 100 mg/kg/day, plus sulfadiazine at 80 mg/L.

Group 7—Rifabutin, 200 mg/kg/day, plus sulfadiazine at 80 mg/L.

Groups 1, 2 and 3 are similar to the three experimental groups discussed and set forth separately in Example 1 and FIG. 1A. For the control group, see Example 1. Results of the experiment are set out in FIGS. 2–4. FIG. 2 shows the results of treatment with low concentrations of rifabutin alone, sulfadiazine alone, or the combination of the two. The effect of sulfadiazine alone was slight, in that only one mouse survived beyond the 9-day period of survival for the control animals. This single mouse died by day 11. The combination of a low dose rifabutin and sulfadiazine was not as effective as the low dose of rifabutin by itself. Only one animal survived beyond day 9 for the combination, with that animal dying on day 13. Four animals survived beyond day 9 for rifabutin alone, the last animal dying on day 14.

Figure 3:
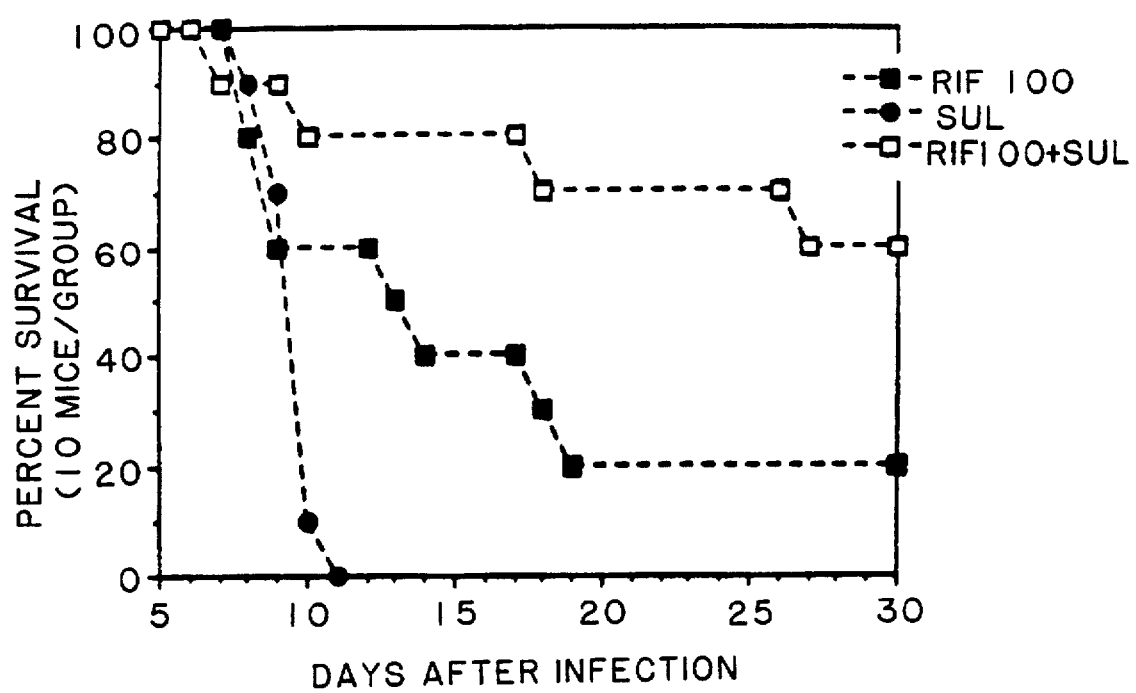
FIG. 3 is a graph showing survival of mice infected with *T. gondii* and treated with moderate concentrations of rifabutin alone or in combination with sulfadiazine.

Higher doses of rifabutin provided greater protection, as shown in FIGS. 3 and 4. There appeared to be a synergistic effect when a dose of rifabutin of 100 mg/kg/day was used in combination with a dose of sulfadiazine of 80 mg/liter (FIG. 3). Six animals survived beyond 9 days when treated with rifabutin alone at a dose of 100 mg/kg/day and 2 animals survived for the entire 30-day period. Surprisingly, 8 of the 10 animals treated with the combination survived beyond 10 days and 6 of them survived for the entire 30-day test period (FIG. 3). As shown in FIG. 4, rifabutin at 200 mg/kg/day was highly effective, and sulfadiazine added to that effectiveness. Nine of the 10 animals survived the entire test period, with rifabutin alone at this concentration, while all 10 survived on the combination.

Example 3

In vivo activity of rifabutin in combination with pyrimethamine against *T. gondii* in a murine model of acute toxoplasmosis An experiment was carried out in the manner described for Examples 1 and 2, but with the additional administration of pyrimethamine instead of a sulfonamide. Pyrimethamine (lot 3F991, Burroughs-Wellcome Co., Research Triangle Park, N.C.) was dissolved in a solution of 0.25% carboxymethylcellulose. Conditions were as described in the first example except for the following changes. Six groups of mice (5 in the control group, 10 or 15 in the treatment groups as indicated in FIG. 5) were infected by intraperitoneal injection of $2.5 \times 10^3$ tachyzoites of *T. gondii*. Treatment with rifabutin alone (50 or 100 mg/kg/day) or in combination with pyrimethamine (10 mg/kg/day) was initiated 24 hours after infection and continued for 10 days. Both drugs were administered orally by gavage as a single daily dose, wither alone or in combination. Test groups were as follows:

Group 1—Control

Group 2—Rifabutin alone, 50 mg/kg/day.

Group 3—Rifabutin alone, 100 mg/kg/day.

Group 4—Pyrimethamine alone, 10 mg/kg/day.

Group 5—Rifabutin, 50 mg/kg/day, plus pyrimethamine, 10 mg/kg/day.

Group 6—Rifabutin, 100 mg/kg/day, plus pyrimethamine, 10 mg/kg/day.

Results of the experiment are set out in FIG. 5. The effects of rifabutin alone are similar to those seen in the previous examples in which average survival rates were extended, with the higher dose giving better long-term protection (30-day test period). The combination of a low dose of rifabutin and pyrimethamine gave better protection than for either drug acting alone. The higher dose of rifabutin in combination with pyrimethamine gave the best protection.

Example 4

Figure 6:
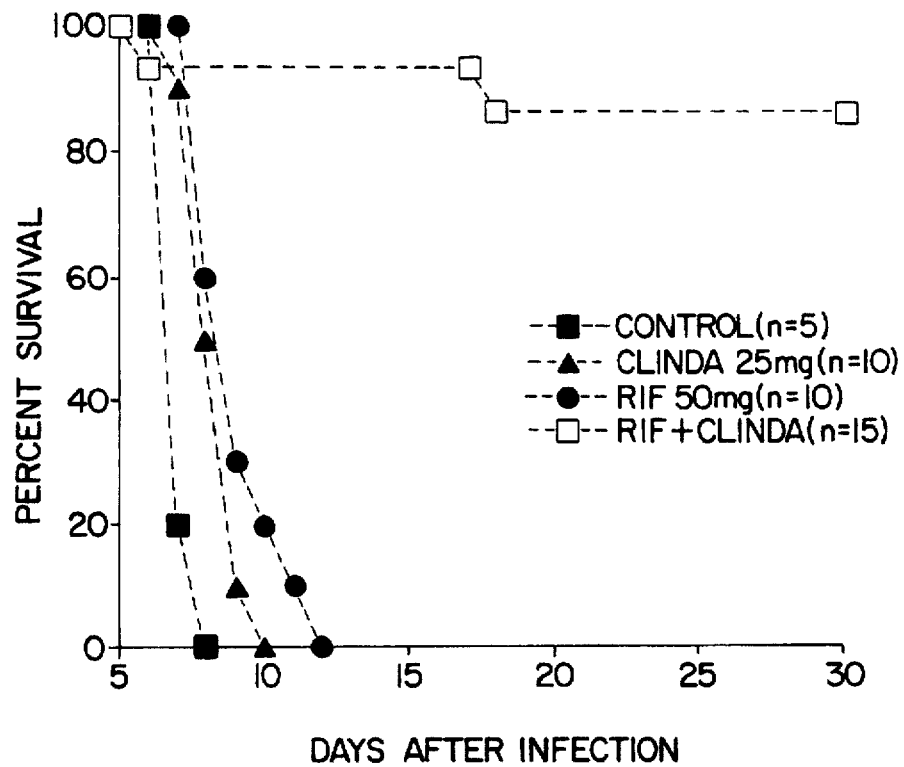
FIG. 6 is a graph showing survival of mice infected with *T. gondii* and treated with rifabutin (RIF) alone or in combination with clindamycin (CLINDA).

In vivo activity of rifabutin in combination with clindamycin against *T. gondii* in an acute model of murine toxoplasmosis Experiments were carried out in the manner described for Examples 1 and 3, but with the additional administration of clindamycin instead of pyrimethamine. Clindamycin (hydrochloride salt, lot 627HJ, Upjohn Co., Kalamazoo, Mich.) was dissolved in sterile PBS and administered orally by gavage in a single daily dose of 25 or 50 mg/kg. Conditions were as described in the first example except for the following changes. Four groups of mice (5 in the control group, 10 or 15 in the treatment groups as indicated in FIG. 6) were infected by intraperitoneal injection of $2.5 \times 10^3$ tachyzoites of *T. gondii* RH strain. Treatment with rifabutin (RIF) alone at 50 mg/kg/day or in combination with clindamycin (CLINDA) at 25 mg/kg/day was initiated 24 hours after infection and continued for 10 days. Both drugs were administered orally by gavage as a single daily dose, either alone or in combination.

Results are shown in FIG. 6. The protection afforded by the combination of rifabutin with clindamycin was remarkable. Ninety percent of mice infected ip with RH tachyzoites survived the infection when treated with a combination of 50 mg/kg of rifabutin plus 25 mg/kg of clindamycin. These doses of the respective drugs had only slight effects in protecting mice against death when administered alone. In a second experiment, 100% of infected mice treated with the combination survived.

Clindamycin is the drug most frequently used as an alternative to sulfonamides when side-effects develop during treatment with the pyrimethamine-sulfonamide combination [34, 35]. The combination of ineffective doses of rifabutin and clindamycin resulted in a synergistic and significant protection of mice with disseminated acute toxoplasmosis.

Example 5

Figure 7A:
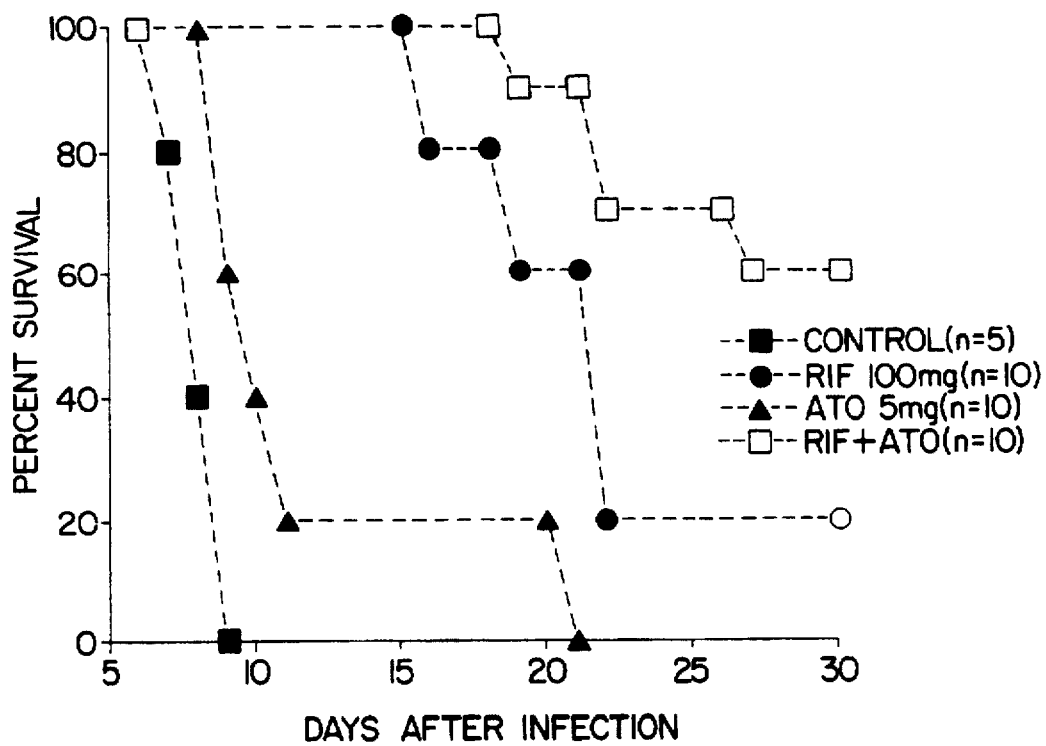

In vivo activity of rifabutin in combination with atovaquone against *T. gondii* in an acute model of murine toxoplasmosis Experiments were carried out in the manner described for Examples 1 and 3, but with the additional administration of atovaquone instead of pyrimethamine. A stock solution of atovaquone (lot 8810001-158, Burroughs-Welcome, Co.) was prepared in PBS and sonicated for 3 pulses of 30 seconds each. Working solutions to provide a dose for each mouse of 5 or 10 mg/kg were prepared in 0.25% carboxymethyl-cellulose and sonicated again for one 30-second pulse just prior to administration by gavage. Conditions were as described in the first example except for the following changes. Four groups of mice (5 in the control group, 10 in the treatment groups as indicated in FIG. 7A and 7B) were infected by intraperitoneal injection of $2.5 \times 10^3$ tachyzoites of *T. gondii* RH strain. Treatment with rifabutin (RIF) alone at 100 mg/kg/day or 50 mg/kg/day or in combination with atovaquone (ATO) at 5 mg/kg/day was initiated 24 hours after infection and continued for 10 days. Both drugs were administered orally by gavage as a single daily dose, either alone or in combination. Control mice were treated with the drug diluent only.

Results are shown in FIGS. 7A and 7B. Treatment with combinations of 50 or 100 mg/kg of rifabutin with 5 mg/kg of atovaquone resulted in protection of mice against death. One hundred mg/kg rifabutin plus 5 mg/kg atovaquone protected at least 60% of the mice against death (FIG. 7A). Statistical analysis of the data, however, did not reveal significant differences between the group of mice treated with rifabutin alone and the group treated with the combination. In contrast, when the dose of rifabutin was reduced to 50 mg/kg and used in combination with a dose of 5 mg/kg/day of atovaquone, prolongation of time to death was obtained, and 30% of the mice survived the infection (FIG. 7B). The difference between the groups of mice treated with rifabutin alone and those treated with the combination was statistically significantly ($P=0.011$).

Since atovaquone is active both against *T. gondii* [30, 31] and *Pneumocystis carinii* [39], and rifabutin is active against mycobacteria, being used for treatment and prophylaxis of organisms of the *Mycobacterium avium* complex [36], the results presented herein, which demonstrate the effectiveness of the combination of rifabutin-atovaquone against *T. gondii*, provide for the use of this combination for treatment and prophylaxis of the three of the most frequently encountered opportunistic agents in AIDS patients.

Example 6

In vivo activity of rifabutin in combination with azithromycin against *T. gondii* in a murine model of acute toxoplasmosis Experiments were carried out in the manner described for Examples 1 and 3, but with the additional administration of azithromycin instead of pyrimethamine. Conditions were as described in the first example except for the following changes. Four groups of adult Swiss-Webster female mice (5 in the control group, 5 or 10 in the treatment groups as indicated in FIG. 8) were infected by intraperitoneal injection of $2.5 \times 10^3$ tachyzoites of *T. gondii* RH strain. Treatment with 50 mg/kg of azithromycin (AZITHRO) or 50 mg/kg of rifabutin (RIF) alone or in combination was administered using a feeding tube, was initiated 24 hours after infection and continued for 10 days. Control mice were treated with drug diluent only.

Results are shown in FIG. 8. One hundred percent of the mice treated with the combination survived at 30 days whereas none of the mice treated with either drug alone survived at 30 days.

Example 7

Figure 9:
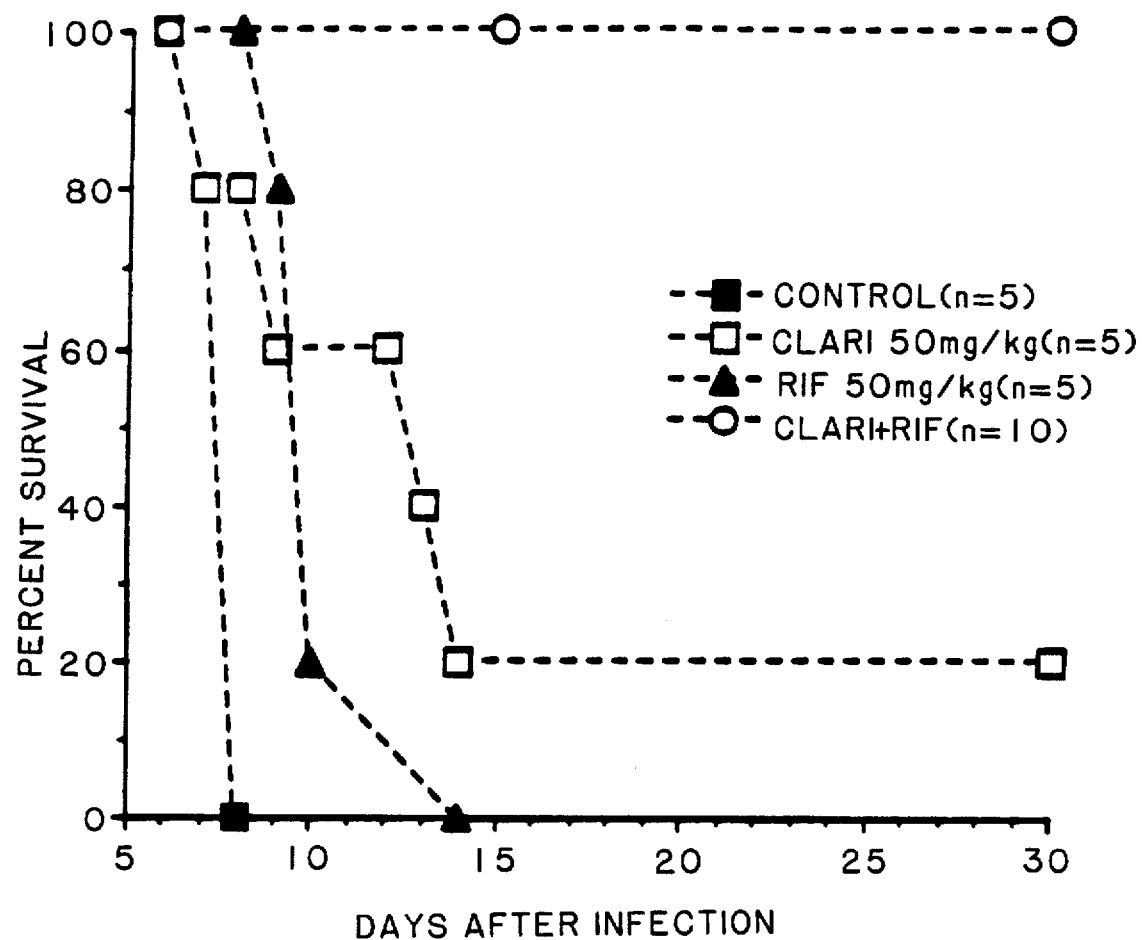
FIG. 9 is a graph showing survival of mice infected with *T. gondii* and treated with rifabutin (RIF) alone or in combination with clarithromycinin (CLARI).

In vivo activity of rifabutin in combination with clarithromycin against *T. gondii* in a murine model of acute toxoplasmosis Experiments were carried out in the manner described for Examples 1 and 3, but with the additional administration of clarithromycin instead of pyrimethamine. Conditions were as described in the first example except for the following changes. Four groups of adult Swiss-Webster female mice (5 in the control group, 5 or 10 in the treatment groups as indicated in FIG. 9) were infected by intraperitoneal injection of $2.5 \times 10^3$ tachyzoites of *T. gondii* RH strain. Treatment with 50 mg/kg of rifabutin (RIF) or 50 mg/kg of clarithromycin (CLARI) alone or in combination was administered using a feeding tube, was initiated 24 hours after infection and continued for 10 days. Control mice were treated with drug diluent only.

Results are shown in FIG. 9. One hundred percent of the mice treated with the combination survived at 30 days whereas 20% of the mice treated with clarithromycin alone survived at 30 days.

Example 8

In vivo activity of rifabutin against *T. gondii* in a murine model of toxoplasmic encephalitis ("TE")

Inbred CBA/Ca (CBA) adult females weighing 17 g at the beginning of each experiment were used to determine rifabutin activity in treatment of toxoplasmic encephalitis caused by infection with cysts of the strain ME49 of *T. gondii* [29, 30]. All mice were purchased from Simonsen Laboratories, Gilroy, Calif. and were fed regular laboratory mouse food and water ad libitum. Each CBA mouse was infected orally with 20 cysts of the ME49 strain [30, 32]. Infected CBA mice were used 5 weeks following infection [37, 39]. Histopathological examination of brains of 3 mice euthanized at this time revealed extensive TE with profuse inflammatory infiltrates in the meninges, parenchyma and around small capillaries as well as large numbers of cysts of *T. gondii*. Rifabutin was dissolved in phosphate buffered saline, pH 6.8, and sonicated for 30 seconds. Treatment with 200 mg/kg of rifabutin administered as a single daily oral dose by gavage was then initiated and continued for 30 days. Five treated and 5 control mice were euthanized by $CO_2$ narcosis 15 and 30 days after initiation of treatment and their brains collected for determination of number *T. gondii* cysts and for histopathologic examination as previously described [30, 32, 41].

Histopathology of brains of control mice 30 days after infection were compared with histopathology of brains of rifabutin treated mice 30 days after infection. Histopathology of brains of control mice treated with the diluent only revealed extensive inflammatory exudates in the meninges, parenchyma and around small capillaries as well as numerous cysts of *T. gondii*. Treatment of infected CBA mice with 200 mg/kg/day of rifabutin administered alone for 15 days did not significantly reduce the inflammatory response or numbers of *T. gondii* cysts in brains of the 5 treated mice as compared with controls. However, treatment with 200 mg/kg/day of rifabutin administered alone for 30 days resulted in remarkable reduction in the inflammatory response in each of the treated mice when compared to controls. The number of *T. gondii* cysts in the brains of the treated mice were not significantly reduced as compared with untreated controls.

These results indicate that rifabutin used alone is effective for treatment of the infection in the central nervous system. Since the numbers of *T. gondii* cysts in the brains of treated mice were not significantly reduced at the end of the therapy, these results may be due to a previously unreported, anti-inflammatory activity of rifabutin. Alternatively, rifabutin may act only against free parasites and/or against rapidly replicating parasites within cells. The drug may not be able to act against the slowly replicating bradyzoites protected within the cyst wall. However, the present invention is not limited by a particular mechanism of rifabutin action.

Example 9

In vivo activity of rifabutin in combination with clindamycin against *T. gondii* in an immunocompromised mammalian host Treatment of a *T. gondii* infected, immunocompromised mammalian host using rifabutin in combination with clindamycin was studied. Immunocompromised T- and B-cell deficient SCID ("severe combined immunodeficient") mice [44] were infected p.o. with cysts of the ME49 strain of *T. gondii*. ME49 cysts are less virulent than C56 cysts, and accordingly are more suitable for studies involving immunocompromised hosts. Clindamycin was dissolved in sterile PBS. Single daily doses of the drug combination, 50 mg/kg of clindamycin with 100 mg/kg of rifabutin, were administered orally by gavage beginning 48 hours after infection. SCID controls were treated with carrier solution only. Mouse mortality was monitored post infection. At day 25 post infection, 100% of infected, immunocompromised mice receiving daily treatments of the combination of 100 mg/kg of rifabutin and 50 mg/kg of clindamycin survived, whereas 100% of the infected, immunocompromised controls died. This is a synergistic effect since these doses of the respective drugs had no effect in protecting immunocompetent mice against death when administered alone under the conditions used in this example. Cessation of the daily drug combination treatment resulted in the death of all the infected, immunocompromised test animals.

In summary, these examples demonstrate the effectiveness of spiropiperidyl rifamycin derivatives, particularly rifabutin, in the protection of a mammalian host, including an immunocompromised host, against infection with *Toxoplasma gondii*. The compounds also demonstrate a synergistic effect in combination with other drugs, particularly with sulfonamides, and provide full protection in this model study against toxoplasmosis.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of reducing the severity of toxoplasmosis resulting from infection of a mammalian host with *Toxoplasma gondii*, which method comprises:

administering to a host in need of said treatment, either after infection or before exposure to said infection, a therapeutically effective amount of a lincosamide in combination with a therapeutically effective amount of a compound that is a spiropiperidyl derivative of rifamycin S, wherein said derivative comprises an imidazole ring that includes carbons at positions 3 and 4 of the rifamycin ring, the carbon at position 2 of said imidazole ring also being a ring carbon at position 4 of a piperidine ring system, thereby forming a spiropiperidyl ring system, said spiropiperidyl ring system optionally comprising a lower hydrocarbon substituent on the nitrogen of said piperidine.

2. The method of claim 1, wherein said compound has a formula

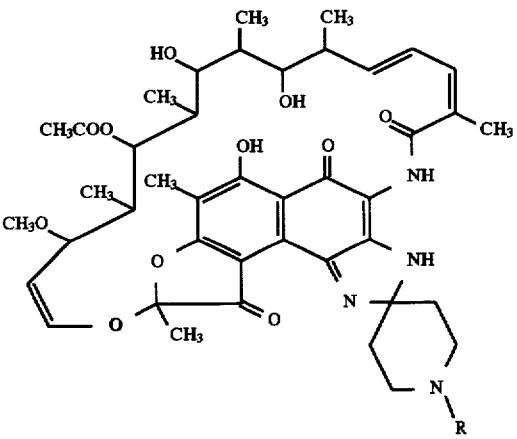

wherein R represents a 3–5 carbon alkyl group.

3. The method of claim 1, wherein said compound is rifabutin.

4. The method of claim 1, wherein said host is an immunocompromised or pregnant human.

5. The method of claim 1, wherein said amount is from 1 to 200 mg/kg/day.

6. The method of claim 1, wherein said administering is by oral ingestion.

7. The method of claim 1, wherein said lincosamide is clindamycin.

* * * * *

UNITED STATES PATENT AND TRADEMARK OFFICE
CERTIFICATE OF CORRECTION

PATENT NO. : 5,665,707
DATED : September 9, 1997
INVENTOR(S) : Jack S. Remington, et al.

It is certified that error appears in the above-identified patent and that said Letters Patent is hereby corrected as shown below:

On the title page, item [54] and column 1, line 4:

In the title of the application, replace "RIFAMYCIK S" with "RIFAMYCIN S"

Signed and Sealed this

Thirtieth Day of December, 1997

Attest:

BRUCE LEHMAN

Attesting Officer

Commissioner of Patents and Trademarks